United States Patent [19]

Nipkow et al.

[11] Patent Number: 5,470,453
[45] Date of Patent: Nov. 28, 1995

[54] REFERENCE ELECTRODE WITH ION BARRIER FOR ELECTROCHEMICAL MEASURING SYSTEMS

[75] Inventors: Andre Nipkow; Eric Bakker, both of Zurich, Switzerland

[73] Assignee: Mettler-Toledo AG, Switzerland

[21] Appl. No.: 971,870

[22] PCT Filed: May 15, 1992

[86] PCT No.: PCT/CH92/00095

§ 371 Date: Jun. 28, 1993

§ 102(e) Date: Jun. 28, 1993

[87] PCT Pub. No.: WO92/21960

PCT Pub. Date: Dec. 10, 1992

[30] Foreign Application Priority Data

May 29, 1991 [CH] Switzerland .................... 1588/91

[51] Int. Cl.$^6$ ............................................ G01N 27/30
[52] U.S. Cl. ...................................... 204/435; 204/400
[58] Field of Search ............................ 204/400, 435, 204/416, 418, 419

[56] References Cited

U.S. PATENT DOCUMENTS

| | | | |
|---|---|---|---|
| 3,190,826 | 6/1965 | Fricke | 204/435 |
| 3,486,997 | 12/1969 | Petersen | 204/435 |
| 3,926,764 | 12/1975 | Ruzicka et al. | 204/435 |
| 4,002,547 | 1/1977 | Neti et al. | 204/435 |
| 5,034,113 | 7/1991 | Iwamoto | 204/435 |
| 5,230,786 | 7/1993 | Preidel | 204/435 |

FOREIGN PATENT DOCUMENTS

| | | |
|---|---|---|
| 0366566 | 5/1990 | European Pat. Off. . |
| 3305962 | 8/1984 | Germany . |
| 2093193 | 8/1982 | United Kingdom . |

*Primary Examiner*—T. Tung
*Attorney, Agent, or Firm*—George Pappas

[57] ABSTRACT

A reference electrode (2) which features an ion barrier (20) based on the redox principle and which is fashioned as an independent unit or as part of a combination electrode, for instance a single-rod measuring chain. Metal ions to be blocked and contained in the reference electrolyte (24) and the material forming the ion barrier (20) together form a redox system. The ion barrier (20) is preferably a reduction agent which reduces the metal ions to the respective metal, and its properties are such that it will not cause contamination of the diaphragm (6) in oxidized state.

8 Claims, 1 Drawing Sheet

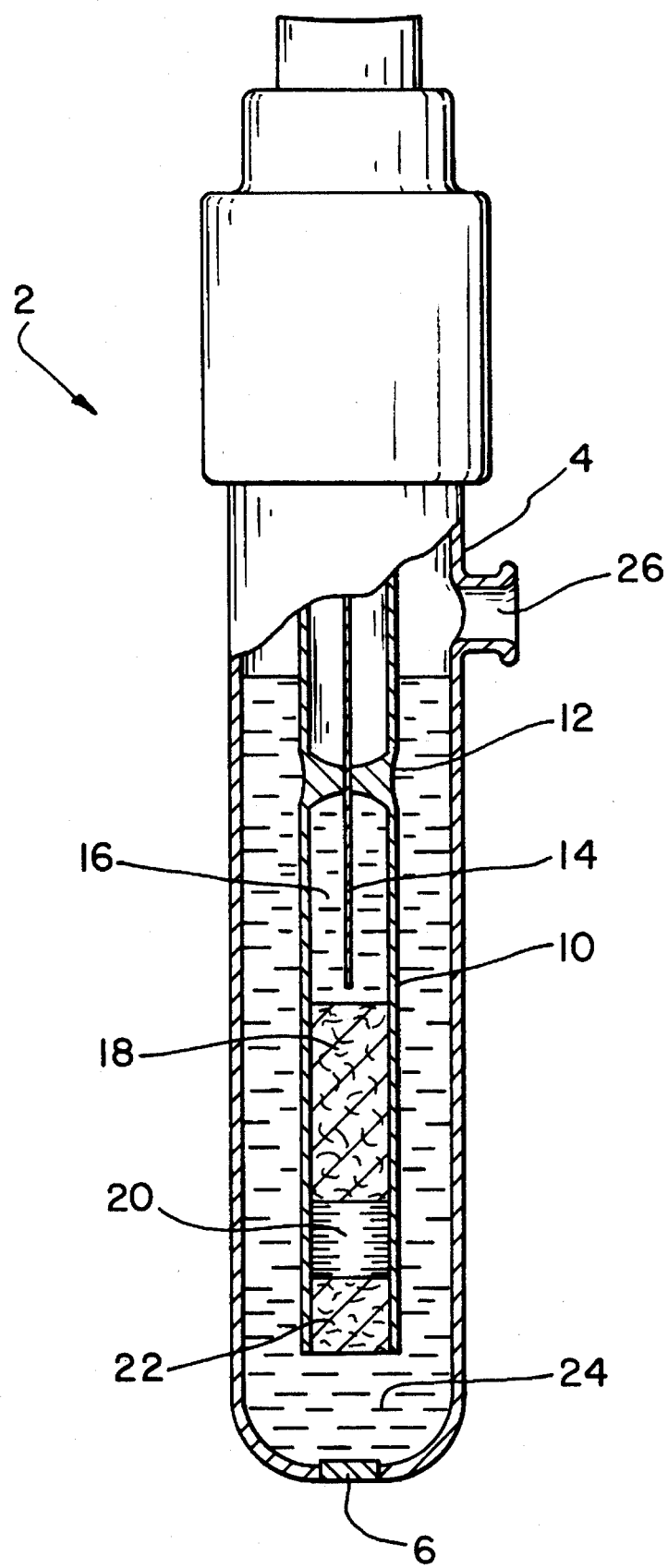

REFERENCE ELECTRODE WITH ION BARRIER FOR ELECTROCHEMICAL MEASURING SYSTEMS

TECHNICAL FIELD

The invention concerns a reference electrode with ion barrier for electrochemical measuring systems.

BACKGROUND OF THE INVENTION

Reference electrodes are electrochemical half cells providing a maximally constant reference voltage. The reference electrode may form an independent unit or may be part of a combination electrode, for instance of a single-rod measuring chain. Besides pH electrodes and ion-selective electrodes, measuring systems for coulometry and polarography are also suitable electrochemical measuring systems.

If the ion-conducting transition between the reference electrode and measured medium takes place through a porous diaphragm, the function of the reference electrode may be impaired by contamination of this diaphragm. The contamination may generate undesirable potentials on the diaphragm, may increase the resistance of the diaphragm, prolong the response time of the reference electrode or impart to it an undesirable selectivity.

Contaminations of the diaphragm may be caused by ingredients of the measured medium, but also by precipitations in which ions from the interior of the reference electrode participate. Silver chloride, relatively soluble at high KCl concentrations, may for instance precipitate on the diaphragm, because the KCl concentration is diluted there by measured solution diffusing into it. The function of the reference electrode may also be impaired by ion precipitations from the reference element with anions from the measured solution, for instance silver sulfide.

To assure a flawless function of the reference electrode and to avoid contaminations in which cations of the reference system, for instance silver ions from the interior of the reference electrode, participate, it is desirable to prevent the migration of such cations to the diaphragm. Toward this objective, various devices have already been developed, which, however, provided only an unsatisfactory solution to this problem. Examples are a) devices reducing the ion transport by convection;

b) devices reducing the diffusion by reversible binding or ion repellency; and c) devices binding the silver ions or silver halogenide complexes irreversibly.

The devices mentioned under (a) include those where the migration of cations to the diaphragm caused by convection, for instance of silver ions, is prevented by providing a diffusion gap between the discharge wire of the reference electrode and the diaphragm. A pertinent example is a single-rod measuring chain developed by the applicant, where, for this purpose, a cotton section is installed. Moreover, known from the German patent document 32 28 647 is the use of a gel- or polymer-fixed reference electrolyte, and from the British patent disclosure 20 93 194 the installation of a bridge electrolyte with a porous diaphragm as a transition to the reference electrolyte.

The effectiveness of the said devices is limited though, since silver ions can in time reach the diaphragm by diffusion.

The devices named under (b) include, for instance, the device described in German patent document 33 05 962, where the diffusion of silver ions to the diaphragm is retarded by installation of ion, cation or anion-cation exchangers to which silver halogenide complexes, for instance $(AgCl_4)^{3-}$, are reversibly bound Moreover these devices include the one known from the British patent disclosure 20 93 193A, where the diffusion is reduced by installation of a microporous polymer to the porous walls of which sulfone groups are bound, since these sulfone groups repel the negatively charged $(AgCl_4)^{3-}$ complexes.

The effectiveness of these devices is limited because the diffusion of silver ions to the diaphragm is not prevented but only reduced. The effectiveness is poor particularly at high temperatures, because the diffusion velocity of the ions increases greatly with the temperature. Thus, it has been found by measurements that a device according to the British patent disclosure 20 93 193A allows, at 80° C., the passage of 38 times as many silver ions as at 25° C.

Contrarily, a complete prevention of the silver ion diffusion to the diaphragm was accomplished by means of the devices named under (c), by installation of ion exchangers to which the silver ions or silver halogenide complexes are irreversibly bound. Devices of that type have been described in German disclosures 34 15 089 and 39 34 302.

Since the effect of these devices is based on a surface effect, their capacity is limited. The disadvantage of these devices is thus to be seen in their limited service life, because—once all of the binding locations of the ion exchanger acting as ion barrier have been occupied—the following cations, for instance silver ions, can diffuse through this ion exchanger to the diaphragm.

The problem underlying the invention, therefore, is to provide a reference electrode where the migration of cations stemming from the interior of the reference electrode, for instance of silver ions, to the diaphragm and consequently its contamination is prevented.

SUMMARY OF THE INVENTION

This problem is solved by means of a reference electrode for electrochemical measuring systems, with a reference electrolyte containing metal ions and with an ion barrier for these metal ions, characterized in that the material forming the ion barrier forms together with the ions contained in the reference electrolyte and to be blocked a redox system.

In the case of this reference electrode, as opposed to known ion barriers which, disregarding convection and diffusion impedance, are based on the principles of ion interaction and ionic binding, the ion barrier works according to the principle of redox processes, i.e., the exchange of electrons. The metal ion contained in the reference electrolyte and to be blocked forms together with the material of the ion barrier, particularly a reduction agent, a redox system. The barrier effect comes about in that the metal ion to be blocked is reduced to metal and precipitated, while the reduction agent is subject to an oxidation reaction.

Suitable reduction agents are, for instance, inorganic or organic redox exchangers or inorganic substances, such as metals, including transition metals, semimetals and alloys, or amalgams.

The reduction agent is preferably so selected that in oxidized state it will not cause any contamination of the diaphragm by undesirable precipitation, so that any risk of contamination for the diaphragm can be precluded.

If the reference electrode is intended for use in biotechnical processes, a reduction agent is suitably selected which in oxidized state forms ions having a toxicity lower than the ions contained in the reference electrolyte and to be blocked, so that in operating state a contamination of the measured medium by toxic ions leaving the ion barrier and the reference electrode can be prevented.

In aqueous solutions, base metals, for instance zinc, tend especially in the presence of protons to form hydrogen, as illustrated by the following equation:

$$Zn + 2H^+ \rightarrow Zn^{2+} + H_2 \uparrow.$$

This reaction is promoted yet if the zinc forms together with the precipitated reduced silver a local element and corrodes electrolytically. To prevent the undesirable hydrogen formation in cases when, for the formation of the redox system, a base metal such zinc is used, where the formation of fine hydrogen bubbles which displace electrolyte from the interstices of the base metal present in the form of a powder is capable of causing an undesirable lowering of the ion conductance, the addition of a basic-reaction metal oxide or earth alkali metal oxide of low solubility to the base metal present in the form of a powder recommends itself.

According to a preferred embodiment of the reference electrode of the initially mentioned type, said electrode is an Ag/AgCl electrode which as the reduction agent forming the ion barrier contains zinc powder with an addition of earth alkali metal oxide.

As already mentioned, the reference electrode may be fashioned as an independent unit or as part of a combination electrode, for instance a single-rod measuring chain.

DESCRIPTION OF THE DRAWINGS

The invention will be more fully explained hereafter with the aid of the drawing and on the example of an Ag/AgCl electrode, the figure showing:

a reference electrode fashioned as an independent unit, partly in section.

DESCRIPTION OF SPECIFIC EMBODIMENTS

The figure illustrates an Ag/AgCl reference electrode 2 with a built-in silver ion barrier. Contained in an electrode interior enveloped by a tubular electrode shaft 4, for instance of glass, equipped with a diaphragm 6 is a one-sidedly open interior tube 10 which in its area away from the diaphragm 6 is sealed by a seal 12. A silver wire 14 extends through this seal into a layer 16 of AgCl powder. Following successively in the direction of the open end of the interior tube 10, starting from the layer 16, are a first cotton section 18, a reduction agent layer 20 formed of zinc powder with an addition of earth alkali metal oxide, and a second cotton section 22 as closure relative to the electrode interior. The electrode interior and the interior tube 10 are filled with a reference electrolyte 24, for instance a 3-molar KCl solution. A filler socket 26 fitted into the electrode shaft 4 is provided for introduction of the reference electrolyte 24.

In the case of the illustrated example of an Ag/AgCl reference electrode with a built-in ion barrier, the surrounding of the silver wire 14 is silver-saturated, so that the silver wire emits a constant voltage. The first cotton section 18, formed by a loosely stuffed cotton wad, reduces the silver ion transport by convection to the silver ion barrier, that is, to the reduction agent layer 20 formed of zinc powder with an addition of earth alkali metal oxide. The silver ions diffusing through the first cotton section 18 are reduced in the silver ion barrier and precipitated as metallic silver, while the zinc is oxidized. The addition of earth alkali metal oxide prevents an undesirable hydrogen formation, which might cause an undesirable lowering of the ion conductance. The second cotton section 22 serves to fix the silver ion barrier in the internal tube 10.

The advantages of a reference electrode with a silver ion barrier of the type described above are constituted by its sterilizability, the stability of the zero point, and its low impedance ($\leq 3k\Omega$). Besides, the service life of the silver ion barrier is practically unlimited, due to its comparatively huge capacity.

Functional Test of the Reference Electrode Described as Example

Silver Ion Emission

When storing a reference element consisting of the components 10 through 22 described in the above example at 80° C. in 5 ml of 3-mol KCl solution as electrolyte, no silver ions were found after 70 days in the electrolyte, using a silver sulfide electrode. Even when the same setup was exposed 50 times to a temperature cycle between 90° C. and 130° C. with a dwell of 30 minutes at 130° C., no silver emission was found. Contrarily, the silver ion concentration in the electrolyte rose in a comparable test setup both after 20 days at 80° C. and after 25 temperature cycles to $>10^{-3}$ mol/liter, when instead of the reaction agent only cotton was filled in.

Zinc Ion Emission

The zinc ion concentration in the electrolyte after the same treatment as described above was always $\leq 4 \times 10^{-7}$ mol/liter and, thus, considerably lower than the silver ion concentration would have been with a reference element without silver ion barrier (silver ion concentration without silver ion barrier: $>10^{-3}$ mol/liter).

Zero Point

The zero point shifts with references elements using a silver ion barrier and such without silver ion barrier after 50 temperature cycles, as described above, were statistically undiscernible.

Impedance

The impedance of reference elements with silver ion barrier fluctuated in the course of 50 temperature cycles between 1 and 3 k$\Omega$. The impedance of control setups without silver ion barrier remained constant at 1 k$\Omega$.

Long-term Performance

Zero point and impedance of reference electrodes with silver ion barrier remained over a period of 5 months at room temperature just as constant as the corresponding values of reference electrodes without silver ion barrier.

Besides the preferred embodiment described with the aid of the example there are still other options for fashioning an effective ion barrier, for instance ion barriers made by means of thin-film or thick-film techniques. For instance, a diffusion layer and a silver ion barrier consisting of a mixture of zinc powder and an ion conduction substrate material can be applied successively, by screen printing, on a planar reference electrode produced by a thick-film technique. There is also the option of applying on the discharge wire of a reference electrode a diffusion layer and a silver ion barrier layer using a dipping technique.

We claim:

1. In a reference electrode for electrochemical measuring systems, including an electrode shaft equipped with a diaphragm and containing a reference electrolyte, an interior tube received within said electrode shaft with a silver wire therein and an ion barrier between said silver wire and said diaphragm, a portion of said reference electrolyte being in contact with said silver wire and said ion barrier, said portion of reference electrolyte containing silver ions, said ion barrier blocking said silver ions by forming a redox system therewith to precipitate said silver ions as silver metal and thereby preventing said silver ions from migrating to said diaphragm.

2. A reference electrode according to claim 1, characterized in that the ion barrier is a reduction agent for the silver ions to be blocked.

3. A reference electrode according to claim 2, characterized in that the reduction agent is an inorganic redox exchanger.

4. A reference electrode according to claim 2, characterized in that the reduction agent is a metal or an amalgam.

5. A reference electrode according to claim 2, characterized in that the electrode is intended for use in biotechnical processes and the reduction agent is so selected that the substance formed upon oxidation of said reduction agent are is not toxic.

6. A reference electrode according to claim 2 characterized in that the electrode is an Ag/AgCl electrode and the ion barrier comprises zinc powder and an earth alkali metal oxide.

7. A reference electrode according to claim 2 characterized in that the ion barrier comprises a mixture of a metal with an earth alkali metal oxide that acts as a base in 3 sol/liter [KCl] KCl.

8. A reference electrode according to claim 2, characterized in that the ion barrier comprises a mixture of a metal with a metal oxide that acts as a base in 3· mol/liter KCl.

* * * * *

UNITED STATES PATENT AND TRADEMARK OFFICE
CERTIFICATE OF CORRECTION

PATENT NO.  : 5,470,453
DATED       : November 28, 1995
INVENTOR(S) : Andre Nipkow et al.

It is certified that error appears in the above-identified patent and that said Letters Patent is hereby corrected as shown below:

Column 2, line 4, after "bound" insert --.--

Column 2, line 4, after "Moreover" insert --,--

COLUMN 6:

Claim 5, line 5, delete "are"

Claim 7, line 15, change "sol" to --mol--

Claim 7, line 15, delete "[KC1]"

Signed and Sealed this

Eleventh Day of June, 1996

Attest:

BRUCE LEHMAN

*Attesting Officer*    *Commissioner of Patents and Trademarks*